United States Patent
Zheng et al.

(10) Patent No.: US 12,319,638 B1
(45) Date of Patent: Jun. 3, 2025

(54) HYPOALLERGENIC ASPARTIC RESIN COMPLEX AND PREPARATION PROCESS THEREOF

(71) Applicant: SHENZHEN FEIYANG PROTECH CORP., LTD, Guangdong (CN)

(72) Inventors: Rulong Zheng, Guangdong (CN); Shuying Zheng, Guangdong (CN); Ping Liang, Guangdong (CN); Zhu Chen, Guangdong (CN); Xiaoyong Qiu, Guangdong (CN); Junle Su, Guangdong (CN)

(73) Assignee: SHENZHEN FEIYANG PROTECH CORP., LTD, Guangdong (CN)

( * ) Notice: Subject to any disclaimer, the term of this patent is extended or adjusted under 35 U.S.C. 154(b) by 0 days.

(21) Appl. No.: 19/000,795

(22) Filed: Dec. 24, 2024

(30) Foreign Application Priority Data

Sep. 13, 2024 (CN) .............................. 202411285484

(51) Int. Cl.
  *C07C 227/08* (2006.01)
  *C08G 63/685* (2006.01)
  *C08K 5/11* (2006.01)
  *C08K 5/17* (2006.01)

(52) U.S. Cl.
  CPC .......... *C07C 227/08* (2013.01); *C08G 63/685* (2013.01); *C08K 5/11* (2013.01); *C08K 5/175* (2013.01)

(58) Field of Classification Search
  None
  See application file for complete search history.

(56) References Cited

U.S. PATENT DOCUMENTS

| | | | |
|---|---|---|---|
| 6,590,066 B1 * | 7/2003 | Roesler | C08G 73/1092 528/335 |
| 10,125,590 B1 * | 11/2018 | Lawson | B01D 17/042 |

FOREIGN PATENT DOCUMENTS

| | | | |
|---|---|---|---|
| CN | 116801445 A | * | 10/2023 |
| WO | WO 2019/211127 A1 | * | 11/2019 |

* cited by examiner

*Primary Examiner* — Tae H Yoon
(74) *Attorney, Agent, or Firm* — Cooper Legal Group, LLC

(57) ABSTRACT

The present application provides a hypoallergenic aspartic resin complex and a preparation process thereof and belongs to a technical field of aspartic resins. The hypoallergenic aspartic resin complex includes the following components: (A) a polyaspartic resin, (B) a monoamine maleate adduct, and (C) diethyl fumarate and/or diethyl maleate, a content of which is not greater than 0.5% by weight in the hypoallergenic aspartic resin complex. The hypoallergenic aspartic resin complex of the present application features a low content of diethyl fumarate and diethyl maleate in percent by weight, no sensitization to human body, and curing performances similar to those of existing polyaspartic resins.

9 Claims, No Drawings

HYPOALLERGENIC ASPARTIC RESIN COMPLEX AND PREPARATION PROCESS THEREOF

CROSS-REFERENCE TO RELATED APPLICATION

The present application claims the priority and benefit of Chinese patent application No. 202411285484.9, filed on Sep. 13, 2024. The entirety of Chinese patent application No. 202411285484.9 is hereby incorporated by reference herein and made a part of this specification.

FIELD OF THE INVENTION

The present application belongs to a technical field of aspartic resins and relates to a hypoallergenic aspartic resin complex and a preparation process thereof.

BACKGROUND OF THE INVENTION

Aspartic resins, usually prepared by Michael addition reaction of dialkyl maleates with organic polyamines, the most commonly used dialkyl maleate is diethyl maleate. In order to promote a more complete reaction of organic polyamides and avoid an influence of residual polyamides on an curing operation time of aspartic resins, excessive diethyl maleate is usually added. However, diethyl maleate will gradually transform into diethyl fumarate with lower reactivity under reaction conditions of synthesizing aspartic resins, and the reactivity of diethyl fumarate is significantly lower than that of diethyl maleate, resulting in a slower reaction rate and an increase in residual diethyl malate and diethyl fumarate. Diethyl maleate and diethyl fumarate have a greater irritant effect on human skin, bronchus and throat mucosa. A content of free diethyl maleate and/or diethyl fumarate in the aspartic resins prepared according to the above method can reach 2 wt % or even higher, resulting in strong sensitization to human skin, bronchus and throat mucosa. A boiling point of diethyl maleate at 1 atmosphere pressure is 225° C., and the content of diethyl maleate and/or diethyl fumarate in aspartic resins cannot be reduced to 2 wt % or less by conventional reduced-pressure distillation. In order to reduce the free diethyl maleate and/or diethyl fumarate in aspartic resins, a short-path distillation process is generally used in the industry to reduce the content of free diethyl maleate and/or diethyl fumarate to 0.5 wt % or less. When the content of diethyl maleate and/or diethyl fumarate in aspartic resins is not greater than 0.5 wt %, an irritation and sensitization to the human body is very low, and it can be considered as no sensitization. However, the short-path distillation process has some problems such as use of expensive equipment, increased production cycle and increased cost, which greatly restricts the application and industry development of aspartic resins.

Therefore, the industry urgently needs to improve current process methods to reduce equipment investment and improve production efficiency, thereby reducing the cost of aspartic resins and controlling the content of diethyl maleate and/or diethyl fumarate in aspartic resins to be no greater than 0.5 wt %.

SUMMARY

In order to solve the above problems, the present application provides a hypoallergenic aspartic resin complex and a preparation process thereof.

Technical solutions of the present application are as follows.

A hypoallergenic aspartic resin complex, including the following components:

(A) a polyaspartic resin with a structure represented by formula (1) below,

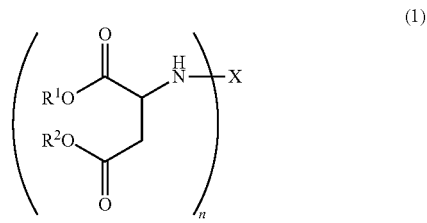

(1)

wherein $R^1$ and $R^2$ are independently selected from C1-C4-alkyls, X is selected from polyvalent organic structures left after removal of primary amino groups of polyamine compounds, the polyvalent organic structures have an average molecular weight of 50-5000 and are inert to isocyanate groups at 100° C., and n=2-3;

(B) a monoamine maleate adduct with a structure represented by formula (2) below,

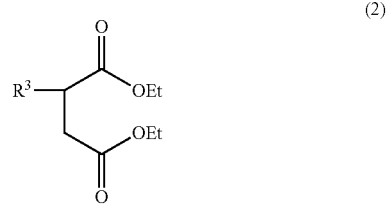

(2)

wherein $R^3$ is selected from organic groups left after removal of one H atom from an amino group in organic amine compounds, the amine compounds contain one primary amino group or one secondary amino group and have a molecular weight of not greater than 150, and Et represents ethyl; and (C) diethyl fumarate and/or diethyl maleate, a content of which is not greater than 0.5% by weight in the hypoallergenic aspartic resin complex.

In some embodiments, the $R^1$ and the $R^2$ are independently ethyl.

In some embodiments, a content of the monoamine maleate adduct in the hypoallergenic aspartic resin complex is 3-15% by weight.

In some embodiments, the organic amine compound is one or more of organic amine compounds with a general chemical formula (3) or (4) below;

wherein $R^4$ is selected from C5-C6-cycloalkyls or C6-C10-substituted cycloalkyls;

wherein $R^5$ and $R^6$ are independently selected from C1-C4-alkyls.

A preparation process for the hypoallergenic aspartic resin complex according to any one of the above embodiments, including the following steps: slowly adding diethyl maleate dropwise to a polyamine compound at a molar ratio of the primary amino group in the polyamine compound to the diethyl maleate being 0.7-0.95:1, and then heating to 40-80° C. for reaction for 48-168 h; then, adding the organic amine compound to obtain a reaction system, and controlling a temperature of the reaction system at 40-100° C. for reaction until a total content of diethyl maleate and diethyl fumarate in the reaction system is not greater than 0.5% by weight; and removing residual low-boiling-point substances by vacuuming at 80° C.-135° C., −0.098 MPa or above, thus obtaining the hypoallergenic aspartic resin complex.

In some embodiments, the molar ratio of the primary amino group in the polyamine compound to the diethyl maleate is 0.8-0.95:1.

In some embodiments, the polyamine compound is one or more selected from a group consisting of: 4,4'-diaminodicyclohexylmethane, 3,3'-dimethyl-4,4'-diaminodicyclohexylmethane, isophorone diamine, 1,6-hexamethylene diamine, 2-methyl-1,5-pentenediamine, 3-methyl-1,5-pentenediamine, 1-methyl-2,4-cyclohexenediamine, 1,3-cyclohexanedimethylamine, 1,2-cyclohexanediamine, 1,3-cyclohexanediamine, 1,4-cyclohexanediamine, 1,3-cyclopentanediamine, o-diamine methylcyclopentane, and polyether amine.

In some embodiments, a molar ratio of the organic amine compound to the diethyl maleate is 0.1-0.5:1.

In some embodiments, a ratio of a total molar number of the primary amino group in the polyamine compound and the organic amine compound to a molar number of the diethyl maleate is 1-1.2:1.

In some embodiments, the organic amine compound is one or more selected from a group consisting of: cyclohexylamine, 2-methylcyclohexylamine, 3-methylcyclohexylamine, 4-methylcyclohexylamine, cyclopentylamine, 2-methylcyclopentylamine, 3-methylcyclopentylamine, dimethylamine, diethylamine, dipropylamine, diisopropylamine, din-butylamine, and diisobutylamine.

Beneficial effects of the present application are as follows.

(1) The present application can reduce the content of diethyl fumarate and/or diethyl maleate in the hypoallergenic aspartic resin complex to 0.5 wt % or less by means of a combination of the monoamine maleate adduct and a conventional aspartic resin.

(2) The present application adopts the method of using insufficient polyamine compound to react with diethyl maleate first, and the reaction is carried out at a relatively low temperature, and a conversion of diethyl maleate to diethyl fumarate during the reaction process can be reduced or avoided by promoting a complete reaction of the polyamine compound; moreover, sufficient or excessive mono-functional organic amine compound is added to react with the remaining unreacted diethyl maleate and/or diethyl fumarate and the reaction is relatively complete, thereby controlling the content of residual diethyl maleate and/or diethyl fumarate to 0.5 wt % or less. Even if the mono-functional organic amine compound is not completely reacted due to excess, because a boiling point of the mono-functional organic amine compound adopted in the present application is relatively low, the mono-functional organic amine compound can be removed by reduced-pressure distillation, and a content of residual mono-functional organic amine compound can be as low as 1% or less, and a curing performance of the hypoallergenic aspartic resin complex of the present application is not affected significantly.

(3) The content of component (B) in the hypoallergenic aspartic resin complex of the present application is low, so the component (B) does not significantly affect a performance of the hypoallergenic aspartic resin complex cured with a curing agent.

DETAILED DESCRIPTION

The technical solutions of the present application is further illustrated and described by specific embodiments below.

The short-path distillation process used in prior art to control the content of diethyl maleate and/or diethyl fumarate in aspartic resins to 0.5 wt % or less has the problems of use of expensive equipment, increased production cycle and increased cost. In order to solve these problems, in a first aspect, the present application provides a hypoallergenic aspartic resin complex. The hypoallergenic aspartic resin complex includes the following components:

(A) a polyaspartic resin with a structure represented by formula (1) below,

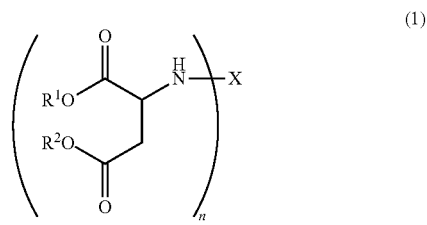

(1)

wherein $R^1$ and $R^2$ are independently selected from C1-C4-alkyls, X is selected from polyvalent organic structures left after removal of primary amino groups of polyamine compounds, the polyvalent organic structures have an average molecular weight of 50-5000 and are inert to isocyanate groups at 100° C., and n=2-3;

(B) a monoamine maleate adduct with a structure represented by formula (2) below,

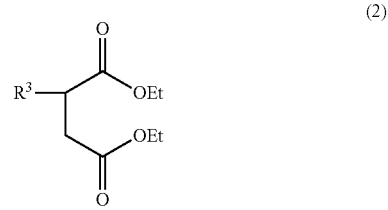

(2)

wherein $R^3$ is selected from organic groups left after removal of one H atom from an amino group in organic amine compounds, the amine compounds contain one primary amino group or one secondary amino group and have a molecular weight of not greater than 150, and Et represents ethyl; and (C) diethyl fumarate and/or diethyl maleate, a content of which is not greater than 0.5% by weight in the hypoallergenic aspartic resin complex.

The hypoallergenic aspartic resin complex of the present application includes the components (A), (B) and (C), and properties of the aspartic resin are mainly reflected by the component (A), namely the polyaspartic resin. The component (B), namely the monoamine maleate adduct, acts as a diluent and by use of the component (B), the content of diethyl fumarate and/or diethyl maleate in the hypoallergenic aspartic resin complex is not greater than 0.5 wt %.

In the present application, the organic amine compound is a mono-functional compound, and a molecule thereof contains only one primary amino group or one secondary amino group. When the organic amine compound contains one primary amino group, the component (B), namely the monoamine maleate adduct, contains one secondary amino group and acts as an active diluent which can participate in a subsequent curing reaction of aspartic resin with a curing agent; when the organic amine compound contains a secondary amino group, the component (B), namely the monoamine maleate adduct, does not contain active H and acts as an inert diluent which cannot participate in the subsequent curing reaction.

In preferred embodiments of the present application, $R^1$ and $R^2$ are independently ethyl, in which case a polyamine compound is subjected to a Michael addition reaction with diethyl maleate.

In preferred embodiments of the present application, a content of the monoamine maleate adduct in the hypoallergenic aspartic resin complex is 3-15% by weight. The monoamine maleate adduct acts as a diluent in the hypoallergenic aspartic resin complex of the present application. Whether it is an active diluent or an inert diluent, too much monoamine maleate adduct will affect a subsequent curing performance of the hypoallergenic aspartic resin complex, such as slow curing or even no curing, and will also reduce a tensile strength and modulus of a curing product and improve a elongation at break. For example, the content of the monoamine maleate adduct in the hypoallergenic aspartic resin complex can be any of 3%, 4%, 5%, 6%, 7%, 8%, 9%, 10%, 11%, 12%, 13%, 14%, 15%, etc., by weight, without special limitations.

In preferred embodiments of the present application, the organic amine compound is one or more of organic amine compounds with a general chemical formula (3) or (4) below;

$$R^4NH_2 \quad (3)$$

where $R^4$ is selected from C5-C6-cycloalkyls or C6-C10-substituted cycloalkyls; for example, $R^4NH_2$ can be cyclohexylamine with a boiling point of about 135° C. at normal pressure, 2-methylcyclohexylamine with a boiling point of about 150° C. at normal pressure, 3-methylcyclohexylamine with a boiling point of about 150° C. at normal pressure, cyclopentylamine with a boiling point of about 107° C. at normal pressure, 4-ethylcyclohexylamine with a boiling point of about 170° C. at normal pressure, 4-propyl cyclohexylamine with a boiling point of about 194° C. at normal pressure, and the like;

$$R^4NHR^6 \quad (4)$$

wherein $R^5$ and $R^6$ are independently selected from C1-C4-alkyls. For example, $R^5NHR^6$ can be dimethylamine, diethylamine, dipropylamine with a boiling point of about 108° C. at normal pressure, diisopropylamine with a boiling point of about 84° C. at normal pressure, di-tert-butylamine, dibutylamine with a boiling point of about 150° C. at normal pressure, and the like.

In a second aspect, the present application further provides a preparation process for the hypoallergenic aspartic resin complex according to any one of the above embodiments, including the following steps: slowly adding diethyl maleate dropwise to a polyamine compound at a molar ratio of the primary amino group in the polyamine compound to the diethyl maleate being 0.7-0.95:1, and then heating to 40-80° C. for reaction for 48-168 h; then, adding the organic amine compound to obtain a reaction system, and controlling a temperature of the reaction system at 40-100° C. for reaction until a total content of diethyl maleate and diethyl fumarate in the reaction system is not greater than 0.5% by weight; and removing residual low-boiling-point substances by vacuuming at 80° C.-135° C., −0.098 MPa or above, thus obtaining the hypoallergenic aspartic resin complex.

In the present application, the diethyl fumarate in the reaction system of the described preparation process is diethyl fumarate transformed from diethyl maleate during the reaction process.

In the above preparation process, when the polyamine compound reacts with diethyl maleate, the polyamine compound is reacted insufficiently relative to diethyl maleate, which can promote the complete reaction of the polyamine compound. By adding sufficient or excessive organic amine compound, the remaining unreacted diethyl maleate can be completely reacted. The total content of diethyl maleate and diethyl fumarate in the product is not greater than 0.5% by weight, and even if the organic amine compound is not completely reacted due to excess, it is easy to remove the residual unreacted organic amine compound by reduced-pressure distillation, and the content of the organic amine compound in the product aspartic resin complex is not greater than 1 wt %. In the present application, in the reaction system or product, the content of the diethyl maleate and/or diethyl fumarate in percent by weight and the content of the organic amine compound in percent by weight may be detected by gas chromatography or high performance liquid chromatography, or the content of the organic amine compound in percent by weight may be detected by gas chromatography and the content of diethyl maleate and/or diethyl fumarate in percent by weight may be detected by high performance liquid chromatography, and specific detection methods can be referred to the prior art "Determination of diethyl maleate by high performance liquid chromatography" (Zhejiang Chemical Industry, 2006, vol. 37, No. 7, 21-22).

In preferred embodiments of the present application, the molar ratio of the primary amino group in the polyamine compound to the diethyl maleate is 0.8-0.95:1. For example, the molar ratio of the primary amino group in the polyamine compound to the diethyl maleate can be any of 0.8:1, 0.82:1, 0.84:1, 0.87:1, 0.87:1, 0.9:1, 0.92:1, 0.92:1, 0.93:1, 0.93:1, 0.93:1, 0.93:1, 0.95:1, 0.95:1, etc., without special limitations.

In preferred embodiments of the present application, the polyamine compound is one or more selected from a group consisting of: 4,4'-diaminodicyclohexylmethane, 3,3'-dimethyl-4,4'-diaminodicyclohexylmethane, isophorone diamine, 1,6-hexamethylene diamine, 2-methyl-1,5-pentenediamine, 3-methyl-1,5-pentenediamine, 1-methyl-2,4-cyclohexenediamine, 1,3-cyclohexanedimethylamine, 1,2-cyclohexanediamine, 1,3-cyclohexanediamine, 1,4-cyclohexanediamine, 1,3-cyclopentanediamine, o-diamine methylcyclopentane, and polyether amine. The polyamine compounds listed above are all polyamine compounds commonly used in the field of aspartic resins containing cycloalkyl in the structure or are polyether amines. The polyether amines can be obtained directly from the market and can be, for example, polyether amine D-230, polyether amine D-400, polyether amine D-2000, polyether amine ED-600, polyether amine ED-900, polyether amine T-403, and polyether amine T-5000, but are not limited thereto.

In preferred embodiments of the present application, a molar ratio of the organic amine compound to the diethyl maleate is 0.1-0.5:1. For example, the molar ratio of the organic amine compound to the diethyl maleate can be any of 0.1:1, 0.12:1, 0.15:1, 0.18:1, 0.2:1, 0.22:1, 0.25:1, 0.27:1, 0.3:1, 0.33:1, 0.35:1, 0.37:1, 0.4:1, 0.42:1, 0.45:1, 0.48:1, 0.5:1, etc., without special limitations.

In preferred embodiments of the present application, a ratio of a total molar number of the primary amino group in the polyamine compound and the organic amine compound to a molar number of the diethyl maleate is 1-1.2:1. By adopting the above technical solution, the diethyl maleate and/or diethyl fumarate in the reaction system can be reacted completely. For example, the ratio of the total molar number of the primary amino group in the polyamine compound and the organic amine compound to the molar number of the diethyl maleate can be any of 1:1, 1.02:1, 1.05:1, 1.07:1, 1.08:1, 1.1:1, 1.12:1, 1.15:1, 1.17:1, 1.18:1, 1.2:1, etc., without special limitations.

In preferred embodiments of the present application, the organic amine compound is one or more selected from a group consisting of: cyclohexylamine, 2-methylcyclohexylamine, 3-methylcyclohexylamine, 4-methylcyclohexylamine, cyclopentylamine, 2-methylcyclopentylamine, 3-methylcyclopentylamine, dimethylamine, diethylamine, dipropylamine, diisopropylamine, din-butylamine, and diisobutylamine. Even if the organic amine compounds listed above which have small molecules, high reactivity with diethyl maleate and/or diethyl fumarate, and low boiling point at 1 atmosphere are used in excess, the organic amine compounds can be removed by simple reduced-pressure distillation, so that the content of the organic amine compounds in the product, namely the hypoallergenic aspartic resin complex, is no greater than 1 wt %, which does not significantly affect the curing performance of the hypoallergenic aspartic resin complex.

The technical solutions of the present application are further described and illustrated in the following examples. Unless otherwise specified, parts used in the following examples means parts by weight.

Example 1

1 mol of 4,4'-diaminodicyclohexylmethane was added into a four necked flask, and 2.2 mol of diethyl maleate was then slowly added dropwise for reaction at 55° C. for 48 h. Then, 0.2 mol of cyclohexylamine was added and a temperature was controlled at 60° C. and held for reaction for 48 h. A reaction product was sampled for high performance liquid chromatography (HPLC) and test results showed that the total content of diethyl maleate and diethyl fumarate was 0.33% by weight. Low-boiling-point substances in the reaction product were removed by vacuuming at 100° C.-105° C., −0.099 MPa and a hypoallergenic aspartic resin complex was obtained. Test results showed that in the complex, the total content of diethyl maleate and diethyl fumarate was 0.38% by weight and a content of cyclohexylamine was 0.1% by weight, and a solid content of the complex was 98.2%.

The solid content was tested under a condition that 2 g of samples were roasted for 2 h in an oven at 105° C.

Example 2

This example is the same as Example 1 except that the amount of cyclohexylamine to be added was adjusted to 0.4 mol from 0.2 mol in Example 1. Test results showed that in the obtained hypoallergenic aspartic resin complex, the total content of diethyl maleate and diethyl fumarate was 0.17% by weight and a content of cyclohexylamine was 0.34% by weight, and a solid content of the complex was 98.4%.

Example 3

1 mol of 4,4'-diaminodicyclohexylmethane was added into a four necked flask, and 2.2 mol of diethyl maleate was then slowly added dropwise for reaction at 55° C. for 48 h. Then, dimethylamine gas was introduced into a result reaction solution by a pipe to keep bubbling until the amount of dimethylamine introduced was about 13.5 g (0.3 mol), the flask was corked tightly, and a temperature was controlled at 50° C. and held for reaction for 96 h. A reaction product was sampled for HPLC and test results showed that the total content of diethyl maleate and diethyl fumarate was 0.18% by weight. Low-boiling-point substances in the reaction product were removed by vacuuming at 80° C.-85° C., −0.099 MPa and a hypoallergenic aspartic resin complex was obtained. Test results showed that in the complex, the total content of diethyl maleate and diethyl fumarate was 0.23% by weight and a content of dimethylamine was 0.02% by weight, and a solid content of the complex was 97.7%.

Example 4

1 mol of 4,4'-diaminodicyclohexylmethane was added into a four necked flask, and 2.2 mol of diethyl maleate was then slowly added dropwise for reaction at 55° C. for 48 h. Then, 0.4 mol of diisobutylamine was added and a temperature was controlled at 75° C. and held for reaction for 128 h. A reaction product was sampled for HPLC and test results showed that the total content of diethyl maleate and diethyl fumarate was 0.07% by weight. Low-boiling-point substances in the reaction product were removed by vacuuming at 130° C.-135° C., −0.099 MPa and a hypoallergenic aspartic resin complex was obtained. Test results showed that in the complex, the total content of diethyl maleate and diethyl fumarate was 0.08% by weight and a content of diisobutylamine was 0.42% by weight, and a solid content of the complex was 97.4%.

Example 5

1 mol of 4,4'-diaminodicyclohexylmethane was added into a four necked flask, and 2.5 mol of diethyl maleate was then slowly added dropwise for reaction at 55° C. for 60 h. Then, 0.6 mol of 2-methylcyclohexylamine was added and a temperature was controlled at 90° C. and held for reaction for 96 h. A reaction product was sampled for HPLC and test results showed that the total content of diethyl maleate and diethyl fumarate was 0.15% by weight. Low-boiling-point substances in the reaction product were removed by vacuuming at 130° C.-135° C., −0.099 MPa and a hypoallergenic aspartic resin complex was obtained. Test results showed that in the complex, the total content of diethyl maleate and diethyl fumarate was 0.22% by weight and a content of 2-methylcyclohexylamine was 0.61% by weight, and a solid content of the complex was 97.8%.

Comparative Example 1

1 mol of 4,4'-diaminodicyclohexylmethane was added into a four necked flask, and 2.1 mol of diethyl maleate was then slowly added dropwise for reaction at 60° C. for 96 h. Vacuuming was performed at 130° C.-135° C., −0.099 MPa for 1 h and an aspartic resin was obtained. The aspartic resin was sampled for HPLC and test results showed that the total content of diethyl maleate and diethyl fumarate in the aspartic resin was 2.4% by weight and the content of diethyl fumarate in the aspartic resin was 2.2% by weight.

Example 6

1 mol of 3,3'-dimethyl-4,4'-diaminodicyclohexylmethane was added into a four necked flask, and 2.4 mol of diethyl maleate was then slowly added dropwise for reaction at 70° C. for 72 h. Then, 0.6 mol of 2-methylcyclohexylamine was added and a temperature was controlled at 90° C. and held for reaction for 100 h. A reaction product was sampled for HPLC and test results showed that the total content of diethyl maleate and diethyl fumarate was 0.10% by weight. Low-boiling-point substances in the reaction product were removed by vacuuming at 130° C.-135° C., −0.099 MPa and a hypoallergenic aspartic resin complex was obtained. Test results showed that in the complex, the total content of diethyl maleate and diethyl fumarate was 0.18% by weight and a content of 2-methylcyclohexylamine was 0.55% by weight, and a solid content of the complex was 98.1%.

Comparative Example 2

1 mol of 3,3'-dimethyl-4,4'-diaminodicyclohexylmethane was added into a four necked flask, and 2.1 mol of diethyl maleate was then slowly added dropwise for reaction at 70° C. for 96 h. Vacuuming was performed at 130° C.-135° C., −0.099 MPa for 1 h and an aspartic resin was obtained. The aspartic resin was sampled for HPLC and test results showed that the total content of diethyl maleate and diethyl fumarate in the aspartic resin was 2.5% by weight and a content of diethyl fumarate in the aspartic resin was 2.4% by weight.

Performance Test Comparison

Polyaspartate coating was prepared according to the following formula.

Component A: consisting of 64% of the hypoallergenic aspartic resin complex or aspartic resin under test, 5% of hydroxyl acrylic resin, 5% of titanium dioxide, 25% of barium sulfate, 0.2% of a dispersant, 0.4% of a defoamer, 0.2% of a leveling agent and 0.2% of an anti-settling agent.

Component B: consisting of 3% of an HDI trimer, 10% of an HMDI and 87% of an adduct curing agent prepared from an IPDI and a polyether polyol.

Polyaspartate coating was obtained by mixing the component A and the component B with a ratio of a total molar content of secondary amine group and hydroxyl group in the component A to a molar content of NCO in the component B being 1:1.05. The polyaspartate coating prepared was made into a film with a thickness of 0.5 mm and cured at 35±2° C. for 15 days, according to test methods and indicators specified in T/CWA204-2021 "Standard for Waterproof Polyaspartate Urea Coatings". Performance test results are shown in Table 1.

TABLE 1

| | Performance data | | | | | | | |
|---|---|---|---|---|---|---|---|---|
| | Example 1 | Example 2 | Example 3 | Example 4 | Example 5 | Comparative Example 1 | Example 6 | Comparative Example 2 |
| Tensile strength/MPa | 17.2 | 17.2 | 16.6 | 16.3 | 17.0 | 17.5 | 15.5 | 15.9 |
| Elongation at break/% | 374 | 370 | 441 | 472 | 425 | 341 | 291 | 257 |
| Tear strength/ N/mm | 98 | 99 | 89 | 83 | 91 | 95 | 90 | 88 |
| Bond strength/ MPa | 14.3 | 14.5 | 13.6 | 13.1 | 14.0 | 13.8 | 12.0 | 11.9 |
| Foldability at low temperature (−35° C.) | No cracks | No cracks | No cracks | No cracks | No cracks | No cracks | No cracks | No cracks |
| Water permeability/ 0.3 MPa, 2 h | Impermeable | Impermeable | Impermeable | Impermeable | Impermeable | Impermeable | Impermeable | Impermeable |
| Pot life/ min | 32 | 32 | 39 | 42 | 35 | 30 | 93 | 90 |
| Surface drying time/ min | 17 | 17 | 23 | 25 | 20 | 15 | 156 | 150 |
| Hard drying time/h | 0.7 | 0.7 | 0.9 | 0.9 | 0.8 | 0.7 | >4 | >4 |

According to the above examples and the results in Table 1, the total content of diethyl maleate and diethyl fumarate in the hypoallergenic aspartic resin of the present application is not greater than 0.5 wt %, and the content of residual organic amine compounds is very low, which does not affect the curing performance of the hypoallergenic aspartic resin significantly.

The basic principles, main features and advantages of the present application are shown and described as above. Those skilled in the art should understand that the present application is not limited by the above examples. The above examples are only preferred embodiments of the present application, and a scope of the present application cannot be limited thereto. That is, equivalent changes and modifications made in accordance with the scope of the present application and contents of the specification should fall within the scope of the present application. The scope of the present application is defined by the appended claims and their equivalents.

What is claimed is:

1. A hypoallergenic aspartic resin complex, comprising the following components:

(A) a polyaspartic resin with a structure represented by formula (1) below,

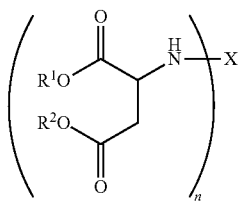

wherein $R^1$ and $R^2$ are independently selected from C1-C4-alkyls, X is selected from polyvalent organic structures left after removal of primary amino groups of polyamine compounds, and the polyvalent organic structures have an average molecular weight of 50-5000 and are inert to isocyanate groups at 100° C., and n=2-3;

(B) a monoamine maleate adduct with a structure represented by formula (2) below,

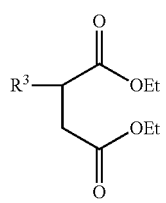

wherein $R^3$ is selected from organic groups left after removal of one H atom from an amino group in organic amine compounds, the organic amine compounds contain one primary amino group or one secondary amino group and have a molecular weight of not greater than 150, and Et represents ethyl; and (C) at least one of diethyl fumarate or diethyl maleate, a content of which is not greater than 0.5% by weight in the hypoallergenic aspartic resin complex;

wherein the organic amine compound is one or more of organic amine compounds with a general chemical formula (3) or (4) below;

wherein $R^4$ is selected from C5-C6-cycloalkyls or C6-C10-substituted cycloalkyls;

wherein $R^5$ and $R^6$ are independently selected from C1-C4-alkyls.

2. The hypoallergenic aspartic resin complex according to claim 1, wherein the $R^1$ and the $R^2$ are independently ethyl.

3. The hypoallergenic aspartic resin complex according to claim 1, wherein a content of the monoamine maleate adduct in the hypoallergenic aspartic resin complex is 3-15% by weight.

4. A preparation process for the hypoallergenic aspartic resin complex according to claim 1, comprising the following steps: slowly adding the diethyl maleate dropwise to a polyamine compound at a molar ratio of the primary amino group in the polyamine compound to the diethyl maleate being 0.7-0.95:1, and then heating to 40-80° C. for reaction for 48-168 h; then, adding the organic amine compound to obtain a reaction system, and controlling a temperature of the reaction system at 40-100° C. for reaction until a total content of the diethyl maleate and the diethyl fumarate in the reaction system is not greater than 0.5% by weight; and removing residual substances by vacuuming at 80° C.-135° C., −0.098 MPa or above, thus obtaining the hypoallergenic aspartic resin complex.

5. The preparation process for the hypoallergenic aspartic resin complex according to claim 4, wherein the molar ratio of the primary amino group in the polyamine compound to the diethyl maleate is 0.8-0.95:1.

6. The preparation process for the hypoallergenic aspartic resin complex according to claim 4, wherein the polyamine compound is one or more selected from a group consisting of: 4,4'-diaminodicyclohexylmethane, 3,3'-dimethyl-4,4'-diaminodicyclohexylmethane, isophorone diamine, 1,6-hexamethylene diamine, 2-methyl-1,5-pentenediamine, 3-methyl-1,5-pentenediamine, 1-methyl-2,4-cyclohexenediamine, 1,3-cyclohexanedimethylamine, 1,2-cyclohexanediamine, 1,3-cyclohexanediamine, 1,4-cyclohexanediamine, 1,3-cyclopentanediamine, o-diamine methylcyclopentane, and polyether amine.

7. The preparation process for the hypoallergenic aspartic resin complex according to claim 4, wherein a molar ratio of the organic amine compound to the diethyl maleate is 0.1-0.5:1.

8. The preparation process for the hypoallergenic aspartic resin complex according to claim 4, wherein a ratio of a total molar number of the primary amino group in the polyamine compound and the organic amine compound to a molar number of the diethyl maleate is 1-1.2:1.

9. The preparation process for the hypoallergenic aspartic resin complex according to claim 4, wherein the organic amine compound is one or more selected from a group consisting of: cyclohexylamine, 2-methylcyclohexylamine, 3-methylcyclohexylamine, 4-methylcyclohexylamine, cyclopentylamine, 2-methylcyclopentylamine, 3-methylcyclopentylamine, dimethylamine, diethylamine, dipropylamine, diisopropylamine, din-butylamine, and diisobutylamine.

* * * * *